United States Patent
Keeling

(10) Patent No.: US 9,750,680 B2
(45) Date of Patent: Sep. 5, 2017

(54) METHODS FOR REDUCING DENTAL STAINING, AND COMPOSITIONS FOR USE THEREIN

(71) Applicant: Akesis Labs, LLC, Bridgeville, PA (US)

(72) Inventor: Gary Keeling, Bridgeville, PA (US)

(73) Assignee: Akesis Labs, LLC, Bridgeville, PA (US)

( * ) Notice: Subject to any disclaimer, the term of this patent is extended or adjusted under 35 U.S.C. 154(b) by 0 days.

(21) Appl. No.: 15/146,706

(22) Filed: May 4, 2016

(65) Prior Publication Data
US 2016/0324759 A1 Nov. 10, 2016

Related U.S. Application Data

(60) Provisional application No. 62/157,377, filed on May 5, 2015.

(51) Int. Cl.
| | | |
|---|---|---|
| *A61K 8/92* | (2006.01) | |
| *A61K 8/24* | (2006.01) | |
| *A61Q 11/00* | (2006.01) | |

(52) U.S. Cl.
CPC .............. *A61K 8/927* (2013.01); *A61K 8/24* (2013.01); *A61K 8/922* (2013.01); *A61Q 11/00* (2013.01); *A61K 2800/80* (2013.01)

(58) Field of Classification Search
USPC ......................................................... 424/49
See application file for complete search history.

(56) References Cited

U.S. PATENT DOCUMENTS

| 4,134,935 A | * | 1/1979 | Quiring | A61K 6/0017 260/998.11 |
| 4,525,342 A | * | 6/1985 | Weiss | A61K 8/67 222/129.4 |
| 8,486,377 B1 | * | 7/2013 | Wrenn | A61K 35/64 424/58 |
| 2007/0269577 A1 | * | 11/2007 | Pershad | A23G 3/343 426/607 |
| 2015/0079010 A1 | * | 3/2015 | Dragan | A61K 8/24 424/57 |

FOREIGN PATENT DOCUMENTS

JP   2001-288025   * 10/2001 ............... A61K 6/00

OTHER PUBLICATIONS

Gucciardi, "Coconut oil is now called a 'miracle' dental bacteria killer." published Feb. 7, 2014 in Overal Health by Get Holistic Health, www.getholistichealth.com.*
Thomas, "Dentists Buzzing About Beeswax." HealthDay Reporter—published Nov. 8, 2001;www.consumer.healthday.com.*

* cited by examiner

*Primary Examiner* — Walter Webb
(74) *Attorney, Agent, or Firm* — Bret E. Field; Bozicevic, Field & Francis LLP

(57) ABSTRACT

Methods and compositions for reducing, (e.g., controlling, inhibiting, preventing, protecting against, or minimizing) staining, (e.g., resulting from stains and/or discoloration) of teeth in the oral cavity are provided. Aspects of the compositions include a component or components (e.g., a wax and an oil) capable of reducing staining of the teeth. In some instances, the compositions further include an agent which enhances the mineralization of teeth.

8 Claims, No Drawings

METHODS FOR REDUCING DENTAL STAINING, AND COMPOSITIONS FOR USE THEREIN

CROSS REFERENCE TO RELATED APPLICATIONS

Pursuant to 35 U.S.C. §119 (e), this application claims priority to the filing date of U.S. Provisional Patent Application Ser. No. 62/157,377 filed on May 5, 2015; the disclosure which application is incorporated herein by reference.

INTRODUCTION

Unblemished white teeth have long been considered cosmetically desirable. Unfortunately, in the absence of thorough dental cleaning, teeth can become discolored or stained from color-causing substances present in food, beverages, tobacco, and the like, and internal sources such as blood, amalgam-based fillings, and antibiotics (e.g., tetracycline). The tooth structures that are generally responsible for presenting a stained appearance are enamel, dentin, and the acquired pellicle. Tooth enamel is predominantly formed from inorganic material, mostly in the form of hydroxyapatite crystals, and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer or matrix that forms continuously over the surface of the tooth. Although the acquired pellicle can be removed through intensive mechanical cleaning, it quickly regenerates soon thereafter.

Discoloration of teeth can result from intrinsic and/or extrinsic staining. Intrinsic staining occurs when staining compounds penetrate the enamel and even the dentin, or alternatively, such staining arises from sources within the tooth. Typically such staining can only be removed through chemical methods of tooth cleaning. In contrast, extrinsic staining of the acquired pellicle arises as a result of compounds such as tannins and other polyphenolic compounds becoming trapped in and tightly bound to the proteinaceous layer on the surface of teeth. Discoloration from this type of staining can usually be removed by mechanical methods of tooth cleaning.

SUMMARY

The present invention relates to a methods and compositions for reducing (e.g., controlling, inhibiting, preventing, protecting against, or minimizing) staining (e.g., the occurrence of stains or discoloration) of teeth in the oral cavity. Aspects of the method include applying a temporary coating composition to the teeth, the composition comprising a safe and effective amount of a component or components capable of minimizing stains, staining, or discoloration of the teeth. The invention also relates to methods and oral compositions which enhance the mineralization of teeth by applying a temporary coating composition to the teeth, the composition comprising a safe and effective amount of a component or components capable of increasing the mineralization level of the teeth.

Compositions employed in methods of the invention may vary. Compositions of interest are capable of coating teeth and may be made up of a variety of components, e.g., waxes, such as bees wax, oils, e.g., coconut oil, and mixtures thereof. The present invention further relates to a method of reducing (e.g., controlling, inhibiting, preventing, protecting against, or minimizing) staining, e.g., as manifested in the occurrence of stains and/or discoloration, of the teeth by applying the above compositions to the teeth of a subject in need thereof. The present invention further relates to a method of providing increased mineralization of teeth by applying the above coating compositions in combination with a mineralization agent to the teeth of a wearer in need thereof.

Aspects of the invention include methods of delivering an anti-stain agent to a selected area of teeth, wherein the area is treated with a temporary coating which binds to and coats the area, followed by contacting the treated area with a beverage, food item, or smoke capable of staining teeth, to enhance anti-staining properties to the area.

In some instances, the temporary coating composition includes a wax, e.g., a bees wax, an oil, e.g., a coconut oil, and mixtures thereof.

The method is useful for reducing (e.g., controlling, inhibiting, preventing, protecting against, or minimizing) staining, e.g., as manifested by the occurrence of stains and/or discoloration of teeth.

The present invention further relates to a method of providing increased mineralization of teeth by applying the above coating composition in combination with a mineralization agent to the teeth of a wearer in need thereof.

Aspects of the invention include oral compositions effective for enhancing the stain-resistant characteristics of teeth. A variety of combinations of modified wax emulsions, coconut oil, beeswax, and various coating compositions are contacted with teeth prior to contacting teeth with an agent or agents capable of staining teeth, to provide enhanced anti-stain properties. The present invention is further directed to methods of making and using the same. Oral compositions effective to promote mineralization of teeth are provided, where the compositions contain a temporary coating composition comprising one or more mineralization agents capable of increasing the mineral content of teeth. Aspects of the invention are further directed to methods of making and using the same.

DETAILED DESCRIPTION

Methods and compositions for reducing, (e.g., controlling, inhibiting, preventing, protecting against, or minimizing) staining, (e.g., resulting from stains and/or discoloration) of teeth in the oral cavity are provided. Aspects of the compositions include a component or components (e.g., a wax and an oil) capable of reducing staining of the teeth. In some instances, the compositions further include an agent which enhances the mineralization of teeth.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It has now been discovered that certain wax and oil mixtures disclosed herein can be used in oral compositions to reduce (e.g., control, inhibit, prevent, protect against, or minimize) staining (e.g., as manifested by the occurrence of stains and/or discoloration) of teeth. The target staining may be a naturally occurring stain, including staining or discoloration caused by smoking, drinking, eating, or taking oral medications.

It has now been discovered that certain wax and oil mixtures that contain an agent capable of increasing the mineral content of teeth disclosed herein can be used in oral compositions to reverse the loss of enamel typically associated with the consumption of acidic beverages and foods, whitening products, and aging.

Aspects of the invention include compositions that reduce (e.g., control, inhibit, prevent, protect against, or minimize) staining, e.g., as manifested by the occurrence of stains and/or discoloration) of teeth.

Aspects of the invention include compositions that are capable of increasing the mineral content of teeth.

Aspects of the invention include effective methods for reducing, (e.g., controlling, inhibiting, preventing, protecting against, or minimizing) staining (e.g., as manifested by the occurrence of stains and/or discoloration) of teeth with compositions of the invention.

Aspects of the invention include effective methods for increasing the mineral content of teeth with the above described compositions.

Aspects of the invention include oral compositions, where the term "oral composition" is used herein to refer to compositions which in the ordinary course of usage are retained in the oral cavity or on the surface of the teeth for a time and manner sufficient to reduce (e.g., control, inhibit, prevent, protect against, or minimize) staining (e.g., as manifested by stains and/or discoloration) of teeth, but are not intentionally ingested. Such products include, for example, waxes, emulsions, liquid and topical solutions.

The present invention relates to an oral composition having reducing, controlling, inhibiting, preventing, protecting against, or minimizing stains, staining, or discoloration of teeth action. The invention relates to a stabilized composition of wax and oil and to methods for use of such a composition. The invention relates in particular to a stabilized composition of wax and oil with an agent capable of adding to the mineral content of teeth enamel and to methods for use of such compositions.

Any convenient wax may be employed. Waxes of interest include natural waxes such as animal, vegetable, and mineral wax. Animal waxes include beeswax, lanolin, shellac wax, Chinese wax, etc. Vegetable waxes include carnauba, candelilla, bayberry, sugar cane, etc., and mineral waxes include fossil and earth waxes (ozocerite, ceresin, montan), and petroleum waxes such as paraffin, microcrystalline, etc. In one embodiment the waxes herein are natural waxes selected from the group consisting of beeswax, candelilla, candela, carnauba, paraffin, microcrystalline wax, Fischer-Tropsch waxes, and mixtures thereof. According to one embodiment of the present invention the wax is derived from bees, i.e., it is a bees wax. Any convenient bees wax may be employed.

Any convenient oil may be employed. Oils suitable for use herein include physiologically acceptable hydrocarbons, vegetable oils, mineral oils, fish oils, animal oils, semi-synthetic and synthetic analogs thereof, and mixtures thereof. Specific oils of interest include corn oil, olive oil, coconut oil, soya bean oil, safflower oil, decane, dodecane, tetradecane, hexadecane, white mineral oil, and mixtures thereof. According to one embodiment of the present invention the oil is derived from coconuts, i.e., it is a coconut oil. Any convenient coconut oil may be employed.

According to one embodiment of the present invention the agent capable of adding to the mineral content of teeth enamel is a calcium phosphate. Calcium phosphate sources of interest that may be present in the compositions include, but are not limited to: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$), ACP (amorphous calcium phosphate or $Ca_3(PO_4)_2 H_2O$), DCP (dicalcium phosphate, monetite or $CaHPO_4$), tricalcium phosphate, including both α- and β-$(Ca_3(PO_4)_2$, tetracalcium phosphate $(Ca_4(PO_4)_2O$, etc. In certain embodiments, wherein a calcium phosphate compound is employed, the ratio of calcium to phosphate (i.e., ratio of calcium cations to phosphate groups) of the compound ranges from 1 to 2.

According to one embodiment of the present invention the agent capable of adding to the mineral content of teeth enamel is a fluoride.

According to one embodiment of the present invention the pH of the oral composition is lowered to the 7.5 to 8.8 range by the addition of bicarbonate or other suitable base agents.

According to another embodiment of the present invention the oral composition reduces, controls, inhibits, prevents, protects against, or minimizes stains, staining, or discoloration of teeth.

According to another embodiment of the present invention the oral composition reduces, controls, inhibits, prevents, protects against, or minimizes stains, staining, or discoloration of teeth that would normally result from the contact of various liquid or solid items with the teeth.

According to another embodiment of the present invention the oral composition reduces, controls, inhibits, prevents, protects against, or minimizes stains, staining, or discoloration of teeth from smoke, wine, tea, dyes, and other stain or color-promoting agents found in the environment.

According to another embodiment of the present invention the amount of bees wax is from about 35% to about 65%, e.g., from about 40% to about 60%, including from about 45 to 55%, by weight of the composition.

According to another embodiment of the present invention the amount of coconut oil is from about 35% to about 65%, e.g., from about 40% to about 60%, including from about 45 to 55%, by weight of the composition.

According to another embodiment of the present invention the oral composition is heated to the temperature range of 62° C.-64° C. (144° F. to 147° F.).

According to another embodiment of the present invention the oral composition is heated to the temperature range of 62° C.-64° C. (144° F. to 147° F.) in order to create a mixture capable of coating teeth.

According to another embodiment of the present invention the oral composition is heated to the temperature range of 62° C.-64° C. (144° F. to 147° F.) and then allowed to cool to room temperature before application to the teeth.

When the oral composition of the present invention is in the form of a solid emulsion, the composition is brought into contact with the teeth. A dose sufficient to form a thin layer of coating on the teeth is sufficient to result in the desired reducing, controlling, inhibiting, preventing, protecting against, or minimizing stains, staining, or discoloration of teeth effect.

When another oral composition of the present invention is in the form of a solid emulsion, the composition is brought into contact with the teeth. A dose sufficient to form a thin layer of coating on the teeth is sufficient to result in the adding of mineral content of teeth enamel effect.

Typical flavoring agents, binders, alcohols, fragrances, abrasives and other excipients known in the art can be added to the compositions of the present invention.

Other Optional Ingredients

Variants of the compositions here include humectant material to keep the emulsion from hardening. Suitable humectants include glycerine, sorbitol, paraffin oil, and the like.

Suitable flavoring agents include flavored oils from botanical or other sources. Sweetening agents can be added including saccharin, stevia, glucose, sucrose, dextrose, levulose, sodium cyclamate, and the like.

Diluents such as mineral oil, saturated aliphatic hydrocarbons, diesters of propylene glycol and triesters of glycerine can be added to variants of the compositions disclosed here.

Thickening agents can be also be added to variants of the compositions disclosed here.

Also provided are kits that at least include the one or more, such as two or more, unit dosages of the composition and which may be used according to the subject methods. The components of the kits may be present in sterile packaging, as desired.

In certain embodiments, the kits which are disclosed herein include instructions, such as instructions for using devices. The instructions for using devices are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging etc.). In other embodiments, the instructions are present as an electronic storage data file present on a suitable computer readable storage medium, e.g., Portable Flash drive, CD-ROM, diskette, cloud, on-line data repository, etc. The instructions may take any form, including complete instructions for how to use the device or as a website address with which instructions posted on the world wide web may be accessed.

The following examples are offered by way of illustration and not by way of limitation.

EXPERIMENTAL

Several representative oral compositions illustrating various embodiments of the invention are set forth in the following examples.

Example I

From about 35% to about 65% by weight of natural bees wax and from about 35% to about 65% by weight of natural coconut oil are heated to the temperature range of 62° C.-64° C. (144° F. to 147° F.) and allowed to cool. A subject applies the resultant mixture to the teeth to form a protective barrier over the teeth prior to smoking, eating, or drinking.

Example II

From about 35% to about 65% by weight of natural bees wax and from about 35% to about 65% by weight of non-natural coconut oil are heated to the temperature range of 62° C.-64° C. (144° F. to 147° F.) and allowed to cool. A subject applies the resultant mixture to the teeth to form a protective barrier over the teeth prior to smoking, eating, or drinking.

Example III

From about 35% to about 65% by weight of non-natural bees wax and from about 35% to about 65% by weight of natural coconut oil are heated to the temperature range of 62° C.-64° C. (144° F. to 147° F.) and allowed to cool. A subject applies the resultant mixture to the teeth to form a protective barrier over the teeth prior to smoking, eating, or drinking.

Example IV

From about 35% to about 65% by weight of non-natural bees wax and from about 35% to about 65% by weight of non-natural coconut oil are heated to the temperature range of 62° C.-64° C. (144° F. to 147° F.) and allowed to cool. A subject applies the resultant mixture to the teeth to form a protective barrier over the teeth prior to smoking, eating, or drinking.

Example V

An agent capable of increasing the mineral content of teeth is added to from about 35% to about 65% by weight of natural bees wax and from about 35% to about 65% by weight of natural coconut oil and the mixture is heated to the temperature range of 62° C.-64° C. (144° F. to 147° F.) and allowed to cool. A subject applies the resultant mixture to the teeth to increase the mineral content of his or her teeth.

Example VI

An agent capable of increasing the mineral content of teeth is added to from about 35% to about 65% by weight of natural bees wax and from about 35% to about 65% by weight of non-natural coconut oil and the mixture is heated to the temperature range of 62° C.-64° C. (144° F. to 147° F.) and allowed to cool. A subject applies the resultant mixture to the teeth to increase the mineral content of his or her teeth.

Example VII

An agent capable of increasing the mineral content of teeth is added to from about 35% to about 65% by weight of non-natural bees wax and from about 35% to about 65% by weight of natural coconut oil and the mixture is heated to the temperature range of 62° C.-64° C. (144° F. to 147° F.) and allowed to cool. A subject applies the resultant mixture to the teeth to increase the mineral content of his or her teeth.

Example VIII

An agent capable of increasing the mineral content of teeth is added to from about 35% to about 65% by weight of non-natural bees wax and from about 35% to about 65% by weight of non-natural coconut oil and the mixture is heated to the temperature range of 62° C.-64° C. (144° F. to 147° F.) and allowed to cool. A subject applies the resultant mixture to the teeth to increase the mineral content of his or her teeth.

Example IX

From about 45% to about 55% by weight of bees wax and from about 45% to about 55% by weight of coconut oil are heated to the temperature range of 62° C.-64° C. (144° F. to 147° F.) and allowed to cool. A subject applies the resultant mixture to the teeth to form a protective barrier over the teeth prior to smoking, eating, or drinking.

Example X

Calcium is added to from about 45% to about 55% by weight of bees wax and from about 45% to about 55% by weight of coconut oil and the mixture is heated to the temperature range of 62° C.-64° C. (144° F. to 147° F.) and allowed to cool. A subject applies the resultant mixture to the teeth to increase the mineral content of his or her teeth.

Example XI

Calcium phosphate is added to from about 45% to about 55% by weight of bees wax and from about 45% to about 55% by weight of coconut oil and the mixture is heated to the temperature range of 62° C.-64° C. (144° F. to 147° F.) and allowed to cool. A subject applies the resultant mixture to the teeth to increase the mineral content of his or her teeth.

Example XII

Fluoride is added to from about 45% to about 55% by weight of bees wax and from about 45% to about 55% by weight of coconut oil and the mixture is heated to the temperature range of 62° C.-64° C. (144° F. to 147° F.) and allowed to cool. A subject applies the resultant mixture to the teeth to increase the mineral content of his or her teeth.

Example XIII

Baking soda is added to from about 45% to about 55% by weight of bees wax and from about 45% to about 55% by weight of coconut oil and the mixture is heated to the temperature range of 62° C.-64° C. (144° F. to 147° F.) and allowed to cool. A subject applies the resultant mixture to the teeth to increase the mineral content of his or her teeth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for reducing staining of a tooth in a subject, the method comprising:
   (i) applying a composition consisting of a bee's wax, a coconut oil, and optionally a mineralizing enhancement agent to the tooth in a manner sufficient to produce a temporary coating of the composition on the coated tooth; and
   (ii) contacting the coated tooth with an agent capable of staining teeth such that staining of the tooth by the agent is reduced.

2. The method according to claim 1, wherein the reducing comprises controlling, inhibiting, preventing, protecting against, or minimizing staining of the tooth.

3. The method according to claim 1, wherein staining is manifested as the occurrence of stains and/or discoloration of the tooth.

4. The method according to claim 1, wherein the composition further includes a mineralizing enhancement agent.

5. The method according to claim 4, wherein the mineralizing enhancement agent comprises a calcium phosphate.

6. The method according to claim 4, wherein the mineralizing enhancement agent comprises a fluoride.

7. The method according to claim 1, wherein the composition is applied in the form of a coating.

8. The method according to claim 1, wherein the agent comprises a beverage, food item, or smoke.

\* \* \* \* \*